United States Patent [19]

Edwards et al.

[11] Patent Number: 4,633,887
[45] Date of Patent: Jan. 6, 1987

[54] ANTI-REFLUX DRAIN TUBE AND DRAINAGE METER COMBINATION

[75] Inventors: Christopher J. Edwards, Bonita, Calif.; Robert D. George, St. Louis, Mo.; Paul Sherlock, San Francisco, Calif.

[73] Assignee: Sherwood Medical Company, St. Louis, Mo.

[21] Appl. No.: 637,464

[22] Filed: Aug. 3, 1984

[51] Int. Cl.⁴ .................. A61B 5/00; B65D 81/00; A61M 1/00
[52] U.S. Cl. .................. 128/762; 128/767; 604/323
[58] Field of Search ............ 128/DIG. 24, 760, 762, 128/766, 771, 767; 138/177, 119, 45, 89; 251/7, 342; 604/34, 250, 322, 323–326

[56] References Cited

U.S. PATENT DOCUMENTS

| | | | |
|---|---|---|---|
| Re. 30,607 | 5/1981 | Manschot et al. | 128/762 |
| 2,694,379 | 11/1954 | Hein | 251/342 |
| 4,178,934 | 12/1979 | Forman | 604/322 |
| 4,301,813 | 11/1981 | Merry et al. | 128/762 |
| 4,305,404 | 12/1981 | Dunn | 128/762 |

Primary Examiner—C. Fred Rosenbaum
Assistant Examiner—J. L. Kruter
Attorney, Agent, or Firm—Stanley N. Garber; Andrew J. Beck; William R. O'Meara

[57] ABSTRACT

A drain tube for urine is connected at its distal end to a urine meter. The tube has a predetermined point of weakness so that when the meter is lifted to dump the urine therefrom, the tube kinks off at the point of weakness, thereby preventing passage of urine from the meter back up the drain tube during dumping. The point of weakness is formed by simultaneously stretching and heating a section of the tube while the inner diameter of the tube is held constant on a mandrel.

14 Claims, 8 Drawing Figures

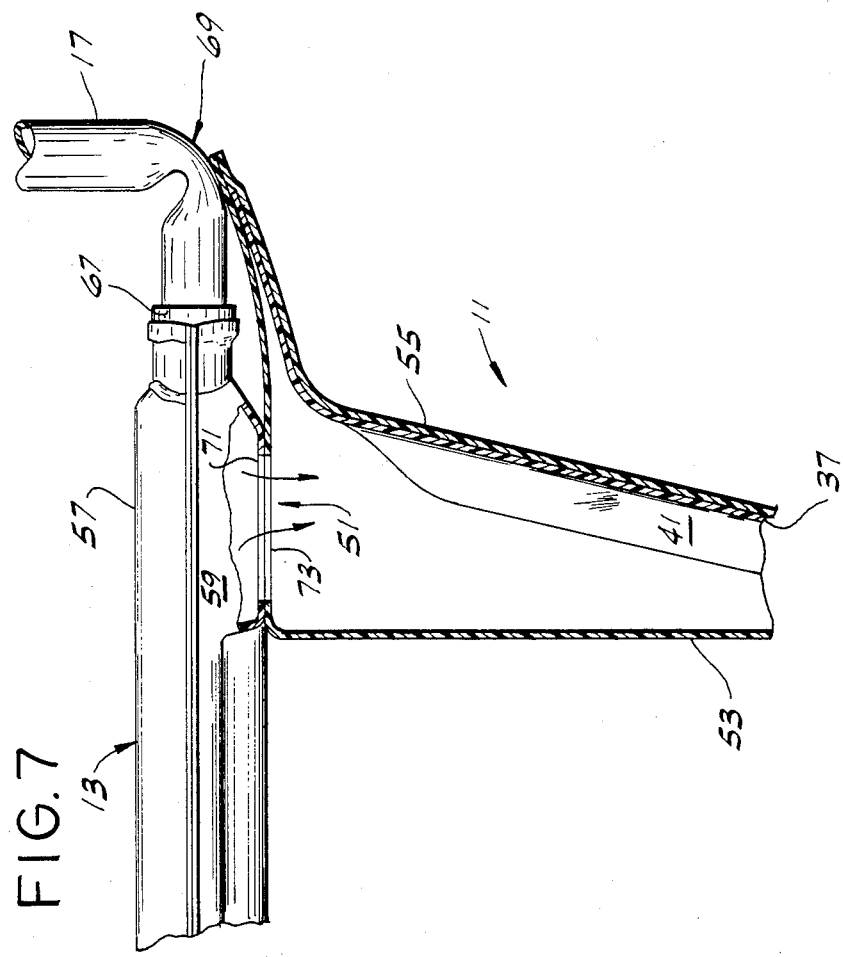
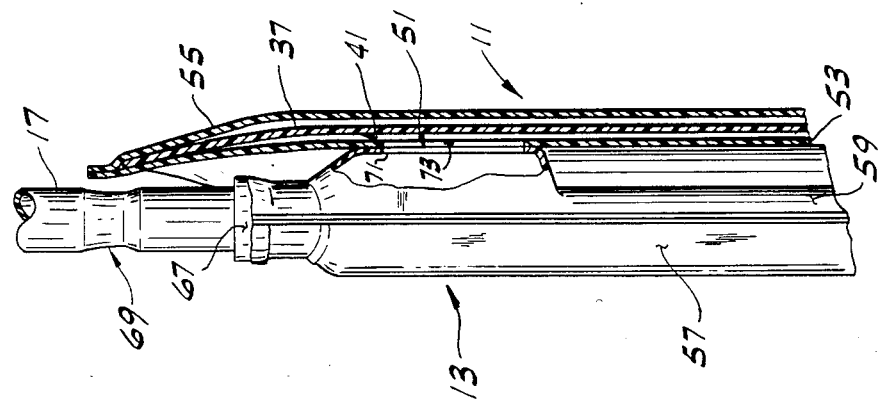

ANTI-REFLUX DRAIN TUBE AND DRAINAGE METER COMBINATION

BACKGROUND OF THE INVENTION

This invention relates to urological apparatus and more specifically to drainage tube and urine meter combinations.

Some typical urine meters consist of a rigid chamber flexibly coupled to a vinyl drainage bag at the upper back surface of the chamber. Such meters are shown in U.S. Pat. No. 4,178,934 to Forman for example. In use, urine is allowed to collect in the chamber where it can be accurately measured. The urine may be manually dumped into the chamber by tilting the chamber upwards, thus allowing the urine to flow by gravity into the bag.

During dumping of such meters, urine may flow back into the inlet tube where it could contaminate urine in the tube, thereby potentially creating an increased incidence of bladder infection and also causing inaccuracy in subsequent measurements of urine in the meter. One possible solution to this problem is to add an anti-reflex valve in line with the drain tube, but this considerably increases the cost and reduces the reliability of the meter.

SUMMARY OF THE INVENTION

It is therefore an object of the present invention to prevent contamination of urine in the drainage tube during dumping, to provide increased accuracy in urine meters, and to minimize the indicence of bladder infection caused by contamination, at an economical cost and with a minimum of parts.

In brief, the drain tube and urine meter combination of this invention includes a relatively rigid meter for collecting and measuring the amount of body fluids passing from a drain tube to an inlet port of the meter. The meter has an outlet port connected to the inlet port of a drainage bag, the meter being manually movable from a substantially vertical position, in which it retains body fluids, to a substantially horizontal position in which the body fluids pass from the outlet port of the meter, through the inlet port of the drainage bag, into the drainage bag for collection therein. The drain tube has a first section extending from the point of connection to the inlet port of the meter longitudinally along the tube a first predetermined distance. The first section of the tube has a substantially constant inner diameter and a first wall thickness. The drain tube also has a second section starting at the end of the first section and extending therefrom longitudinally along the tube a second predetermined distance much shorter than the first predetermined distance. The second section of the tube has a wall thickness at at least one point along its length which is substantially less than the wall thickness of the first section. A third section of the tube extends longitudinally from the second section of the tube toward the proximal end of the tube. The wall thickness of the third section of the tube is at least as large as the wall thickness of the first section and substantially greater than the wall thickness of the second section. Upon manual movement of the meter from its vertical to a substantially horizontal position, the walls of the tube preferentially collapse together at the second section to prevent flow of the body fluids from the meter past the second section of the tube while the meter is in the substantially horizontal position.

The method of making a drain tube of the present invention includes the steps of providing a first section of the tube extending a first predetermined length longitudinally along the tube from the distal end, the first section having a first wall thickness, and forming a second section of the tube extending a second predetermined length longitudinally along the tube. The second predetermined length is much less than the first predetermined length and the wall thickness of the second section is much less than the wall thickness of the first section. The method includes the further step of providing a third section of the tube extending from the second section longitudinally along the tube toward the proximal end thereof. The third section has a wall thickness at least as great as the wall thickness of the first section and substantially greater than the wall thickness of the second section.

Other features and objects of the invention will be in part apparent and in part pointed out hereinafter.

BRIEF DESCRIPTION OF THE DRAWINGS

FIG. 6 is a sectional view on an enlarged scale taken along lines 6—6 of FIG. 1 with the bottom portion broken away;

FIG. 7 is a view similar to FIG. 6 but showing the urine meter in its vertical position.

Similar reference characters indicate similar parts throughout the several views of the drawings.

DESCRIPTION OF THE PREFERRED EMBODIMENT

Figure 1:
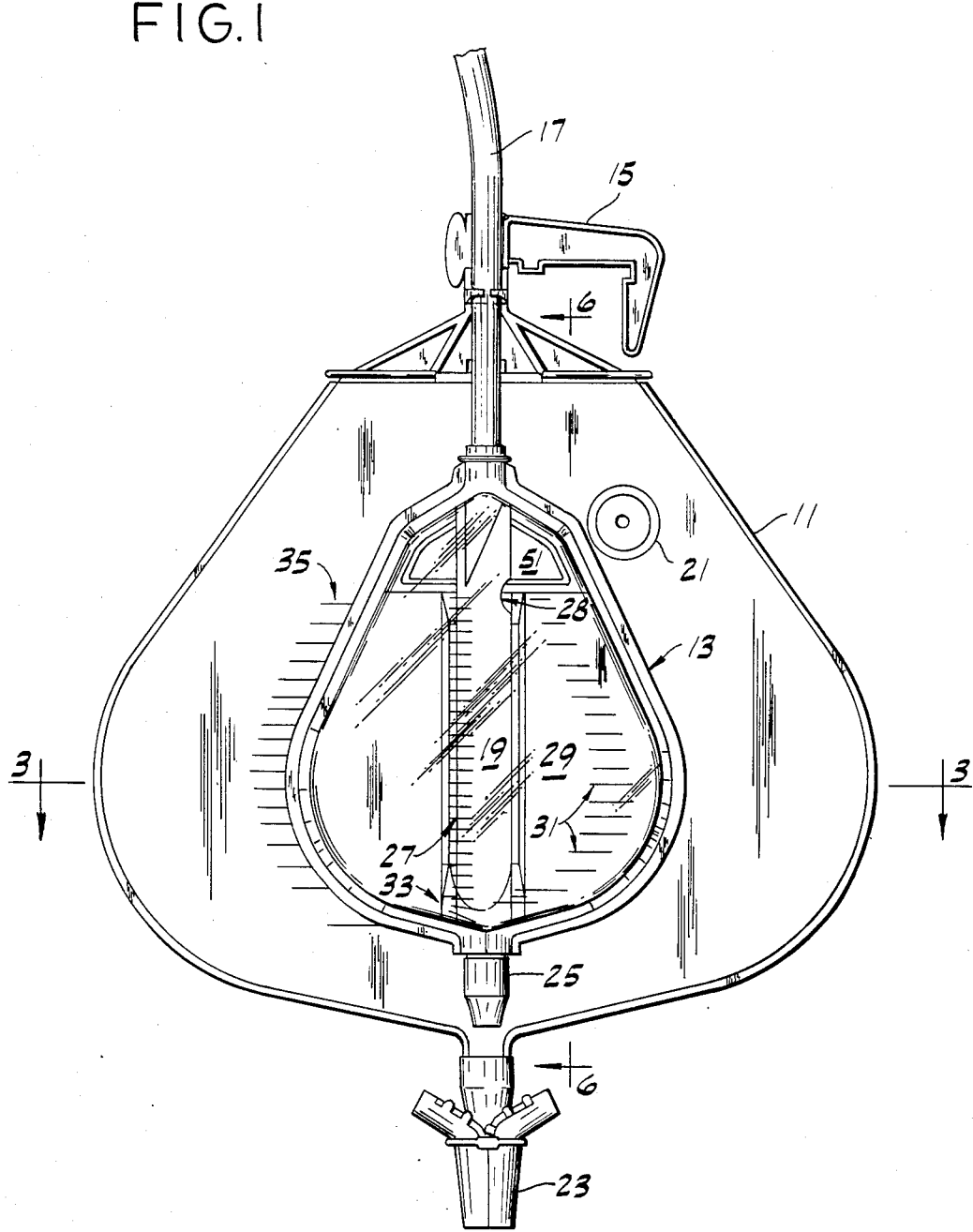
FIG. 1 is a front elevation of a urine meter, drain tube and drainage bag combination of this invention.

Turning now to the drawings, there is shown in FIG. 1 a flexible urinary drainage bag 11 in combination with a relatively rigid urine metering collection chamber or urine meter 13. Bag 11 is suitably secured, by radio frequency sealing or the like, to a drainage bag support 15 such as is disclosed in co-assigned U.S. patent application Ser. No. 520,954 filed Aug. 5, 1983 so that in use bag 11 may be suspended vertically from a hosptial bed or the like (not shown) to collect body fluids, e.g. urine, from a patient. Specifically, body fluid such as urine flows through a drain tube 17, which terminates at its proximal end with an inclined cut, into a burette 19 disposed inside and constituting part of meter 13. Bag 11 also has a vent 21 of conventional design secured by radio frequency sealing or the like in the front thereof to pemit the expulsion of air from bag 11 as the bag is filled with urine. At the lower end of the bag 11 is a manually actuable value 23 which when open provides a path for urine to exit from the interior of bag 11. Meter 13 similarly has a manually operable valve 25 at its lower end for the same purpose.

Figure 8:
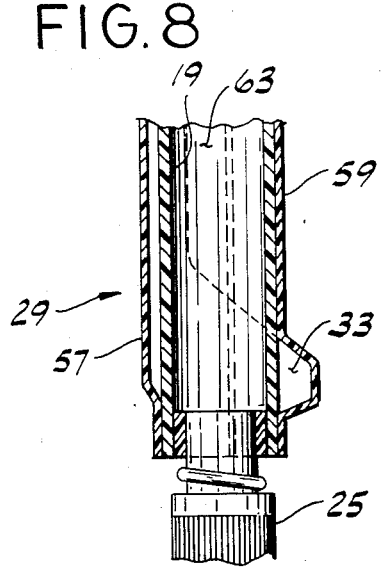
FIG. 8 is a sectional view taken along lines 8—8 of FIG. 4.

Burette 19 preferably is an extruded, relatively flexible tube of a plastic such as polyvinyl chloride (PVC). By way of example, burette 19 can have an outside diameter of about 0.75 inch (1.9 cm) and a wall of approximately 0.05 inch (1.5 mm). The burette extends from the bottom of meter 13 to generally the top thereof (approximately 6 inches (15.3 cm) for example) and is sealed at the bottom thereof to the body of the meter and valve 25 so that urine entering the burette from drain tube 17 fills burette 19 from the bottom without leaking out. Burette 19 can thus be used in conjunction with a set of gradations 27 printed or otherwise permanently affixed to the transparent vinyl (PVC) front of meter 13 to provide accurate measurement of a relatively small amount of urine, e.g. two to thirty ml. As urine fills the burette to or approaching the uppermost of gradations 27, it spills out of an opening 28 in burette 19 into the main body, labelled 29, of meter 13. Also printed or otherwise affixed on the face of meter 13 is a second set of gradations 31 which permit the measurement of somewhat larger amounts of urine, e.g. 35 to 200 ml in the main body of the meter. As is best seen in FIG. 8, a passage 33 is provided in main body 29 behind burette 19 to ensure that urine levels in the main body of the meter on both sides of the burette are equal, so that the measurement given by gradations 31 is accurate.

For convenience, the front of bag 11 is also transparent or translucent, is preferably calendared, and has printed or otherwise affixed thereon a third set of gradations 35, so that the amount of urine in the bag itself, as opposed to in the meter, may be at least approximately measured in increments of, for example, from approximately 100 ml to approximately 1800 ml.

Figure 2:
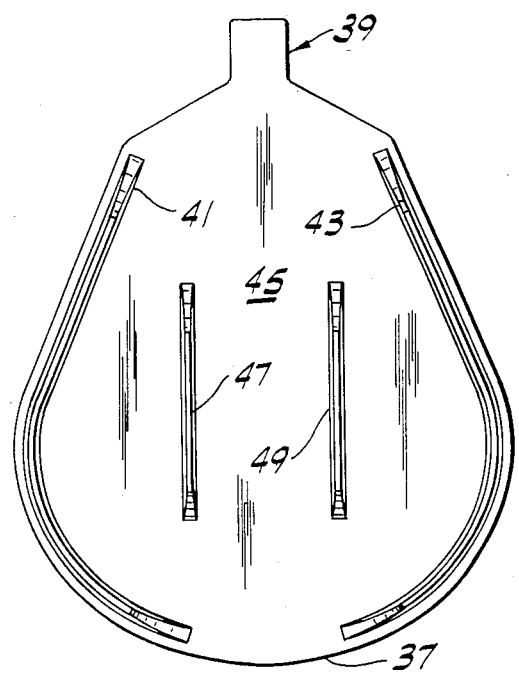
FIG. 2 is a front elevation of a spacer which is preferably disposed in the combination of FIG. 1.
Figure 4:
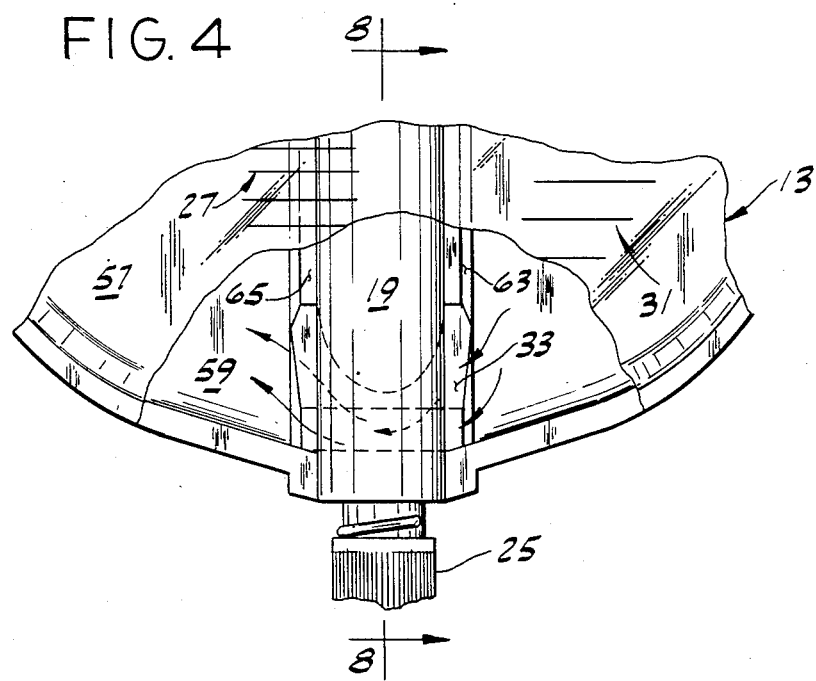
FIG. 4 is a front elevation, on an enlarged scale and with parts broken away, of the lower portion of the combination of FIG. 1.

A spacer 37 (FIG. 2) of relatively rigid polyvinyl chloride material having a thickness of approximately 0.01 inch (0.25 mm) is provided for inclusion inside bag 11. At its top spacer 37 includes a tab 39 suitable for radio frequency sealing or the like to the top of bag 11 to hold spacer 37 in place inside the bag. Along its left and right peripheries, spacer 37 includes a pair of ribs 41, 43 which extend generally perpendicularly approximately 0.5 inch (12.5 mm) out from the main body, labelled 45, of spacer 37. The size and shape of spacer 37 and the placement of ribs 41 and 43 is selected so that the urine meter seats between ribs 41 and 43. Spacer 37 also includes a second pair of ribs 47, 49 extending generally perpendicularly approximately 0.3 inch (8 mm) out from main body 45, ribs 47 and 49 being generally paralled to the longitudinal axis of spacer 37. Ribs 47 and 49 are shorter in length than ribs 41 and 43 and, as best seen in FIG. 4, terminate at their upper end in the vicinity of an inlet port or opening 51 of bag 11.

Figure 3:
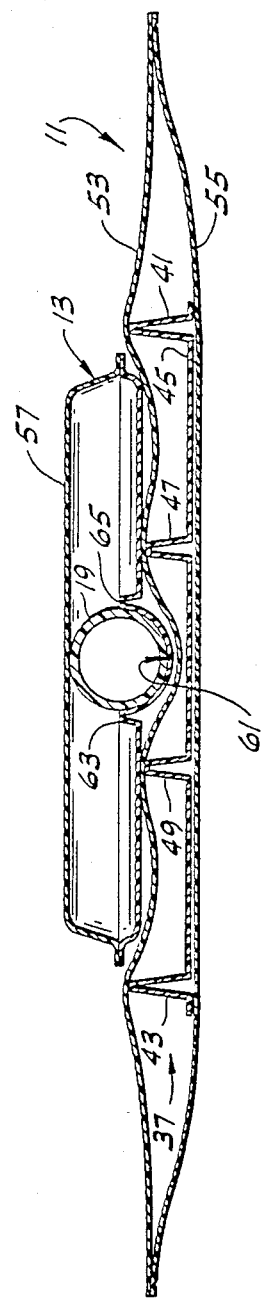
FIG. 3 is a sectional view on an enlarged scale taken along lines 3—3 of FIG. 1.

The lower portion of bag 11, meter 13, burette 19 and spacer 37 are shown in section in FIG. 3. Bag 11 is seen to have a relatively flexible, transparent front panel 53 of calendared vinyl (PVC) having a thickness of approximately 0.01 inch (0.25 mm) suitably secured as by radio frequency sealing at its periphery to a relatively flexible, opaque rear panel 55 of vinyl PVC of approximately the same thickness, said rear panel preferably being white to contrast with any urine in bag 11. Spacer 37 is disposed inside bag 11, i.e. between panels 53, 55 with ribs 41 and 43 being disposed exteriorly of meter 13. Ribs 47 and 49, on the other hand, can come into contact with the rear of meter 13 through front panel 53 of bag 11. Ribs 47 and 49 are not as tall (do not extend out from the body of spacer 37 as far) as ribs 41 and 43, thereby reducing the overall width of the bag and meter combination from what it would be if ribs 47 and 49 were as tall as ribs 41 and 43.

Meter 13 has a transparent, relatively rigid front panel 57 of vacuum formed polyvinyl chloride and an opaque, preferably white, rigid rear panel 59, also of vacuum formed polyvinyl chloride, which panels are suitably sealed together such as by radio frequency sealing along their edges, each panel having a thickness of approximately 0.025 inch (0.6 mm). Rear panel 59 has formed therein a recess or groove 61 and a pair of ribs 63, 65 to receive and support flexible burette tube 19 against transvere movement. The ribs also strengthen the meter itself and maintain the circular cross-section of the burette. Ribs 63 and 65 terminate short of the bottom of meter 13 (see FIG. 4) and channel 33 is formed in rear panel 59 (see FIG. 8) to permit urine to freely flow behind burette 19 to equalize the urine levels in each half of meter 13. Referring back to FIG. 3, front panel 57 supports burette 19 as well by being in frictional contact therewith even though the front panel is not molded to receive the burette.

Figure 5:
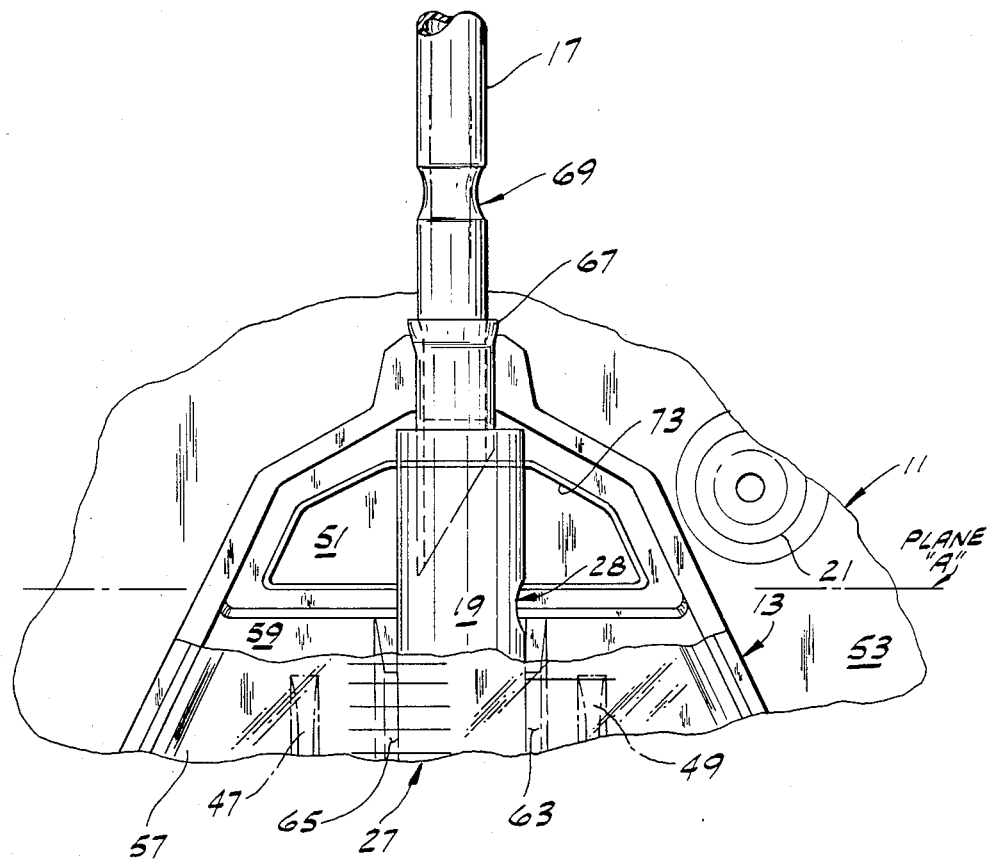
FIG. 5 is a front elevation, on an enlarged scale and with parts broken away, of the upper portion of the combination of FIG. 1.

The tops of meter 13 and burette 19 are shown in greater detail in FIG. 5. Drain tube 17 is secured in the top of meter 13 in a clear plastic bushing 67 of PVC whose inclined lower end terminates in burette 19 and which is itself secured by a suitable adhesive or sealing process to the top of meter 13. Relatively rigid panels 57 and 59 extend around bushing 67 and help hold it in place. The inclined proximal end of bushing 67 thus constitutes the inlet port of meter 13. Tube 17 extends generally from the inlet port of meter 13 upwardly a predetermined distance to a section thereof labelled 69 which has a length much shorter than the predetermined distance. At section 69 the wall of tube 17 has been thinned to provide a predetermined point of weakness. This thinning, which is exaggerated in FIGS. 5-7, is accomplished without changing the inner diameter of tube 17, which diameter remains substantially constant throughout its length by, for example, placing the proximal portion of the tube over a mandrel and rotating it about its longitudinal axis while simultaneously heating section 69 and stretching the tube. By way of example, the inner diameter of tube 17 throughout its length is approximately 0.3 inch (8 mm) while the outer diameter can vary from 0.4 inch (1 cm) above and below section 69 to approximately 0.36 inch (9 mm) at section 69. However, even this much thinning of the wall is not necessary. All that is required is that the wall be thinned enough at section 69 to make section 69 the weakest part of the tube 17 so that when bent, the tube will kink off at that point.

The purpose of section 69 is illutrated in FIGS. 6 and 7. Rear panel 59 of urine meter 13 has an outlet port 71 molded therein with a lip 73 thereof which extends into and is suitably secured to front panel 53 of bag 11. As urine fills meter 13 to the bottom of outlet port 71, the urine spills over lip 73 through inlet port 51 of bag 11 into the bag. Many times, however, the meter is not allowed to become this full. Rather, periodically a nurse records the amount of urine in meter 13 and then rotates meter 13 from its generally vertical portion of FIG. 6 around plane A (FIG. 5) to a substantially horizontal position shown in FIG. 7 to dump the contents of the meter into the bag. Section 69, being the point of weakness, thereupon kinks off tube 17. This action closes the lumen of tube 17 and ensures that the urine passes into bag 11 instead of traveling up tube 17.

When the urine is dumped into bag 11, spacer 37 and specifically ribs 41, 43, 47 and 49 hold walls 53 and 55 of the bag apart to promote rapid dumping of the urine into the bag. The calendared texture of front panel 53 also promotes rapid dumping as it reduces the tending of the front and rear panels of the bag to stick together.

In view of the above it will be seen that the objects of the invention are achieved and other advantageous results attained.

Although the invention has been described with reference to the preferred embodiment illustrated in the drawings, many modifications will be apparent to those skilled in the art without departing from the spirit or scope of this invention.

What is claimed is:

1. A body drainage fluid metering and collection assembly comprising a drainage collection container having an inlet port in an upper portion thereof, a relatively rigid meter chamber for collecting and measuring body drainage fluid having inlet and outlet ports, said meter chamber outlet port being connected in fluid communication with said container inlet port, and flexible drain tube means for connection at one end with a patient source of drainage fluid and connected at the opposite end with said meter chamber inlet port for transfering drainage fluid from the source to said meter chamber, said meter chamber being connected to and manually movable from a substantially vertical position in which drainage fluid is collected and retained therein toward a horizontal position in which drainage fluid can pass from said meter chamber outlet port through said container inlet port and into said container for collection therein, said drain tube means having a first tube section spaced from said meter chamber inlet port, and a second tube section external to said meter chamber and said container and connected between said first tube section and said meter chamber, said second tube section being less resistant to bending substantially transversely to the longitudinal axis of said tube means than said first tube section so that upon movement of said meter chamber from the substantially vertical position toward a horizontal position said second tube section bends substantially transversely of the longitudinal axis thereof and closes said second tube section.

2. The assembly of claim 1 wherein the bottom end of said second tube section is above said meter chamber outlet and said collection container inlet port.

3. The assembly of claim 1 wherein the wall thickness of said second tube section at at least one point thereon is substantially less than the wall thickness of said first tube section.

4. The assembly of claim 3 wherein said tube includes a third tube section having a wall thickness greater than that of said second tube section, sid third tube section being connected between said second tube section and said meter chamber inlet.

5. The assembly of claim 4 wherein the inner diameters of said first, second and third tube sections are all substantially the same.

6. The assembly of claim 4 wherein said first section has a substantially constant inner diameter, said second section has a substantially shorter longitudinal length than said first section, the wall thickness of said third section being at least as large as the wall thickness of said first section.

7. The assembly of claim 4 wherein said meter chamber and said second and third tube sections extend vertically and are normally substantially straight when said meter chamber is in said vertical position.

8. A urine metering and collection assembly comprising a urine collection container for collecting a relatively large amount of urine and having an inlet port in an upper portion thereof, a relatively rigid urine meter chamber for collecting and measuring a relatively small amount of urine having inlet and outlet ports, said meter chamber outlet port being in an upper portion of said meter chamber and connected in fluid communication with said container inlet port, and a flexible urine drain tube for connection at one end with a patient source of urine and connected at the opposite end with said meter chamber inlet port, said meter chamber connected to and manually movable from a substantially vertical position in which urine is collectd and retained therein toward a horizontal position in which urine can pass from said meter outlet port through said container inlet port and into said container for collectiion therein, said drain tube having a first tube section spaced from said meter chamber inlet port, and a second tube section being external to said meter chamber and said container and substantially less resistant to bending than said first tube section so that it bends more easily transversely to the longitudinal axis of said tube than said first tube section, said second tube section being predeterminately spaced longitudinally along said tube from said inlet port between said inlet port and said first tube section such that upon predetermined movement of said meter chamber from the substantially vertical position toward a horizontal position said second tube section bends substantially transversely of the longitudinal axis thereof and closes said second tube section to prevent urine flow in said tube past said second tube section while urine is flowable from said meter chamber to said container.

9. The assembly of claim 8 wherein the wall thickness of said second tube section is substantially less than that of said first section.

10. The assembly of claim 9 wherein the inner diameters of said first and second tube sections are substantially the same.

11. The assembly of claim 8 wherein said tube has a third section connected between said second section and said meter chamber inlet, said first, second, and third tube sections have substantially the same inner diameters, and said second section has a wall thickness less than that of said first and third sections.

12. The assembly of claim 11 including means for maintaining said second and third tube sections substantially when said meter chamber is in a vertical position.

13. The assembly of claim 8 wherein the wall thickness of said second and third sections are substantially the same and the inner diameter of said tube is substantially constant along its length.

14. A urine metering and collection assembly comprising a urine collection container having an inlet port in an upper portion thereof, a relatively rigid meter chamber connected to said container for movement relative thereto for collecting and measuring urine and having inlet and outlet ports, said meter chamber outlet port being connected in fluid communication with said container inlet port, and flexible drain tube means for connection at one end with a patient source of urine and connected at the opposite end with said meter chamber inlet port for transferring urine from the source to said meter chamber, said meter chamber being connected to and manually movable from a substantially vertical position in which urine is collected and retained therein toward a horizontal position in which urine can pass from said meter chamber outlet port through said container inlet port and into said container for collection therein, said drain tube means having a first tube section connected to said meter chamber inlet port, and a second tube section external to said meter chamber and said container and connected to said first tube section, said first tube section being connected between said second tube section and said meter chamber inlet port, said second tube section being less resistant to bending substantially transversely to the longitudinal axis of said tube means than said first tube section so that upon movement of said meter chamber from the substantially vertical position toward a horizontal position said second tube section bends substantially transversely of the longitudinal axis thereof and closes said second tube section.

* * * * *